United States Patent [19]

Hayashi et al.

[11] Patent Number: 4,529,594
[45] Date of Patent: Jul. 16, 1985

[54] PROTEIN HAVING ANTITUMOR ACTIVITY

[75] Inventors: Hiroshi Hayashi, Fuji; Junji Kuwashima, Toyonaka, both of Japan

[73] Assignees: Asahi Kasei Kogyo Kabushiki Kaisha; Dainippon Pharmaceutical Co., Ltd., both of Osaka, Japan

[21] Appl. No.: 629,853

[22] Filed: Jul. 11, 1984

[30] Foreign Application Priority Data

Jul. 15, 1983 [JP] Japan .............................. 58-127779

[51] Int. Cl.[3] ...................... C07G 7/00; A61K 35/14; A61K 37/00
[52] U.S. Cl. ................................. 514/12; 260/112 R; 260/112 B; 260/112.5 R; 424/85; 424/88; 424/101
[58] Field of Search ........ 260/112 R, 112 B, 112.5 R; 424/177, 101, 85, 88

[56] References Cited

U.S. PATENT DOCUMENTS

| | | | |
|---|---|---|---|
| 4,076,701 | 2/1978 | Burton et al. | 260/112 B |
| 4,309,418 | 1/1982 | Green | 424/177 |
| 4,390,468 | 6/1983 | Sasaki et al. | 260/112 R |
| 4,405,608 | 9/1983 | Moody et al. | 260/112.5 R X |
| 4,447,355 | 5/1984 | Sakamoto et al. | 260/112 B |
| 4,457,863 | 7/1984 | Kawai et al. | 260/112 R |

OTHER PUBLICATIONS

Proc. Nat. Acad. Sci., U.S.A., 72 (9), 3666–3670, (1975), Carswell et al.
Proc. Nat. Acad. Sci., U.S.A., 73 (2), 381–385, (1976), Green et al.
Expl. Cell Biol., 47, 53–60, (1979), Helson et al.
Brit. J. Cancer, 38, 302–309, (1978), Matthews et al.
Brit. J. Cancer, 42, 416–422, (1980), Matthews et al.
Infect. Immun., 28 (1), 204–211, (1980), Mannel et al.
Infect. Immun., 30 (1), 159–164, (1980), Anderson et al.
Infect. Immun., 33 (2), 527–530, (1981), Fernandes et al.
J. Immunol., 125, 1671–1677, (1980), Ruff et al.
Brit. J. Cancer, 44, 418–424, (1981), Matthews.
J. Immunol., 126 (4), 1279–1283, (1981), Kull et al.
J. Natl. Cancer Inst., 59 (5), 1519–1522, (1977), Green et al.
Infect. Immun., 33 (2), 523–526, (1981), Oseas et al.
Infect. Immun., 33 (1), 156–164, (1981), Mannel et al.

*Primary Examiner*—Howard E. Schain
*Attorney, Agent, or Firm*—Pennie & Edmonds

[57] ABSTRACT

A protein having a polypeptide subunit containing an N-terminal amino acid sequence of Ser-Ala-Ser-Arg-Ala-Leu-Ser-Asp-Lys-Pro-Leu-Ala-His-Val-Val-Ala-Asn-Pro-Gln-Val-Glu-Gly-Gln-Leu-Gln-Trp-Leu. The protein of the present invention is obtained in substantially pure form at high activity recovery, and is excellent in inducing necrosis of tumors with no toxicity upon the normal tissues of the living body. The protein of the present invention is thermally stable and, therefore, when preparation of pharmaceutical compositions is conducted, the protein of the present invention can be stably formulated into compositions.

5 Claims, No Drawings

PROTEIN HAVING ANTITUMOR ACTIVITY

This invention relates to a novel protein having an antitumor activity. More particularly, the present invention is concerned with a protein comprising a polypeptide subunit having a specific N-terminal amino acid sequence. The present invention is also concerned with a substantially pure protein having an antitumor activity comprising the polypeptide subunit having the N-terminal amino acid sequence described herein, and pharmaceutical compositions containing the protein having an antitumor activity as the active ingredient.

In the present specification, amino acids and peptides are represented using abbreviations, as indicated below, approved by IUPAC-IUB Commission on Biochemical Nomenclature (CBN). Incidentally, with respect to amino acids and the like having optical isomers, those represented by the following abbreviations are of the L-configuration unless otherwise specified.

Ala: alanine residue
Arg: arginine residue
Asp: aspartic acid residue
Glu: glutamic acid residue
Gln: glutamine residue
Gly: glycine residue
His: histidine residue
Leu: leucine residue
Lys: lysine residue
Pro: proline residue
Ser: serine residue
Trp: tryptophan residue
Val: valine residue There are known various substances having a capacity for stimulating the reticuloendothelial system, for example, substances having physiological activities such as tumor cell-killing activity which are induced by various Gram-positive bacteria and endotoxins. Specifically, Carswell et al discovered that the serum from CD-1 Swiss mice infected with bacillus Calmette-Guérin (BCG), and after two weeks, followed by intravenous injection of endotoxin has cytotoxic activity against cultured L cells and also discovered a phenomenon that it induces hemorrhagic necrosis of Meth A sarcoma transplanted in the (BALB/c×C57BL/6)F$_1$ mouse. They gave the name of TNF (Tumor Necrosis Factor) to the active substance in the serum [Proc. Nat. Acad. Sci., USA, 72,3666–3670 (1975)]. Thereafter, Ruff et al reported that the rabbit TNF prepared according to the above-mentioned method proposed by Carswell et al was purified about 2,000-fold over the serum ]J. Immunol., 125, 1671–1677 (1980)]. Further, Matthews et al reported that the rabbit TNF was purified about 1,000-fold over the serum [Br. J. Cancer, 42, 416–422 (1980)]. However, in Ruff et al and Matthews et al, the tumor necrosis effect with respect to the purified TNF is not confirmed in animal experiments.

Japanese Patent Application Laid-Open Specification No. 57-140725 (1982) discloses a process for isolating and purifying a proteinaceous physiologically active substance having antitumor activity, which is induced by administering to a mammal such as mouse, rabbit or guinea pig at least one substance having a capacity for stimulating the reticuloendothelial system and then injecting endotoxin from a Gram-negative bacterium into the mammal, or by adding endotoxin from a Gram-negative bacterium to a tissue culture containing activated macrophages from a mammal. In this Japanese Patent Application Laid-Open Specification, there are also disclosed the molecular weight and isoelectric point of the purified proteinaceous physiologically active substance (molecular weight, 39,000±5,000 in terms of a value as measured by gel filtration and SDS-polyacrylamide gel electrophoresis; isoelectric point, pH 3.9±0.3 in terms of a value as measured by isoelectric focusing). Although the above-mentioned proteinaceous physiologically active substance has an excellent antitumor activity, it is disadvantageous that the activity recovery (the terminology "activity recovery" used herein will be explained later), of the substance, attained by the purification is low.

The present inventors have made extensive and intensive studies on a purification method for obtaining the above-mentioned proteinaceous substance at high activity recovery. As a result, the present inventors have unexpectedly found that by a method different from the purification method described in the above-mentioned Japanese Patent Application Laid-Open Specification, a novel proteinaceous substance which is different from the above-mentioned substance and has an excellent antitumor activity can be obtained at high activity recovery, namely, at an activity recovery as high as about 50 to 70% through purification. The present invention has been made based on such a novel finding.

Therefore, it is an object of the present invention to provide a novel protein having an antitumor activity.

In one aspect of the present invention, there is provided a protein having an antitumor activity comprising a polypeptide subunit having an N-terminal amino acid sequence of the following formula (I):

Ser-Ala-Ser-Arg-Ala-Leu-Ser-Asp-Lys-Pro-Leu-
Ala-His-Val-Val-Ala-Asn-Pro-Gln-Val-Glu-Gly-
Gln-Leu-Gln-Trp-Leuwherein Ala stands for alanine residue, Arg an arginine residue, Asn an asparagine residue, Asp an aspartic acid residue, Gln a glutamine residue, Glu a glutamic acid residue, Gly a glycine residue, His a histidine residue, Leu a leucine residue, Lys a lysine residue, Pro a proline residue, Ser a serine residue, Trp a tryptophan residue and Val a valine residue;

and which protein has:

(a) a molecular weight of 40,000±5,000 in terms of a value as measured by a gel filtration method as defined herein and a molecular weight of 17,500±2,000 in terms of a value as measured by an SDS-polyacrylamide gel electrophoresis method as defined herein; and (b) an isoelectric point of 5.0±0.3 in terms of a value as measured by an isoelectric focusing method as defined herein.

The protein having an antitumor activity of the present invention (hereinafter often referred to as "present substance" also) is essentially characterized by its polypeptide subunit having an N-terminal amino acid sequence of the following formula (I):

Ser-Ala-Ser-Arg-Ala-Leu-Ser-Asp-Lys-Pro-Leu-
Ala-His-Val-Val-Ala-Asn-Pro-Gln-Val-Glu-Gly-
Gln-Leu-Gln-Trp-Leu-    (I)

which was initially determined as being:

Ser-Ala-Ser-Arg-Ala-Leu-Ser-Asp-Lys-Pro-Leu-
Ala-His-Val-Val-Ala-Asn-Pro-Gln-Val-Glu-Gly-
Gln-Leu-Gln-X-Leuwherein Ala stands for alanine residue, Arg an arginine residue, Asn an asparagine residue, Asp an aspartic acid residue, Gln a glutamine residue, Glu a glutamic acid residue, Gly a glycine residue, His a histidine residue, Leu a leucine residue, Lys a lysine residue, Pro a proline residue, Ser a serine residue, Trp a tryptophan residue, Val a valine residue, and X one amino acid residue.

The present substance is also characterized in that it has a molecular weight of 40,000±5,000 in terms of a value as measured by a gel filtration method as defined herein and a molecular weight of 17,500±2,000 in terms of a value as measured by an SDS-polyacrylamide gel electrophorisis method as defined herein, and an isoelectric point of 5.0±0.3 in terms of a value as measured by an isoelectric focusing method as defined herein. In addition to the above-mentioned properties, the present substance has the following properties:

(i) a specific cytotoxic activity against L-M cells is $5 \times 10^6$ to $1 \times 10^7$ units/mg-protein in terms of a value as measured by item (4) of the property-determining methods as will be mentioned later;

(ii) an activity of inducing a hemorrhagic necrosis of Meth A sarcoma transplanted in mice is (+) or higher level in terms of a value as measured by item (5) of the property-determining methods as will be mentioned later when the present substance is intravenously administered to mice in an amount of 3000 to 5000 units/mouse;

(iii) in the electrophoresis using a cellulose acetate membrane, the present substance forms a band in the same region as in that of α-globulin;

(iv) the present substance is not adsorbed to a column packed with various lectins [Con A-Sepharose, WGA-Sepharose 6MB, RCA-I-Gel, UEA-I-Gel and LPA-I-Gel]. This fact shows that the present substance hardly contains a sugar-chain; and (v) the biological activity of the present substance is not lost by the treatment with 1 mM of dithiothreitol or 2-mercaptoethanol.

The terminology "biological activity" used herein is intended to mean the cytotoxic activity against L-M cells in terms of a value as measured by item (4) of the property-determining methods as will be mentioned later.

The properties of the protein of the present invention are measured according to the following property-determining methods, items (1) to (9).

ITEM (1) DETERMINATION OF N-TERMINAL AMINO ACID SEQUENCE

First, in order to prepare a sample for determining an amino acid sequence, the protein of the present invention is subjected to preparative electrophoresis.

Using an apparatus SJ-1060 SDH type (manufactured and sold by Atto Corp., Japan), SDS-polyacrylamide gel plates (150×110×1 mm) containing 15% polyacrylamide are prepared with reference to a pamphlet "slab type SDS-polyacrylamide gel electrophoresis" published by Atto Corp., Japan.

Ten lanes are provided on one gel plate and 40 μg of the present substance is applied to each lane. In this instance, a pretreatment is effected, that is, 500 μl of an aqueous solution containing 400 μg of the present substance is mixed with 100 μl of 1% SDS aqueous solution and 50 μl of 40% sucrose aqueous solution and then, subjected to heat treatment at 50° C. for 30 minutes. The electrophoresis is completed at a constant voltage of 150 V within 4.5 hours. After completion of the electrophoresis, one of the lanes is stained with Coomassie Brilliant Blue G-250 for 5 minutes, thereby to detect a clearly-stained protein band. Then the remaining lanes are cut into 2.5 mm slices and each slice is extracted with 1.5 ml of 1% ammonium bicarbonate at 4° C. for 24 hours. The extract is taken with a Pasteur pipette, and each slice is washed with 1% ammonium bicarbonate. Thus, 2.5 ml of the extract is obtained from each gel slice. Each extract is subjected to the assay of cytotoxic activity against L-M cells to affirm which extract contains the present substance. The activity of the present substance is found only in the slices having the same Rf value as that of the clearly-stained protein band.

The electrophoresis as mentioned above is effected five times to obtain 1.6 mg of a sample extract from 2 mg of the material charged.

The sample extract thus obtained is applied onto a column (0.9×10 cm) of Sephadex G-25 to effect desalting. The resultant is dried at 25° C. for 2 hours, using a centrifugal vacuum drying type concentrator EC-10 (manufactured and sold by Tomy Seiko Co., Ltd. Japan) at 1,500 rpm. Thus, there is provided a sample for determination of the amino acid sequence of the present substance.

Using an amino acid sequence analyzer Model 470 A (Applied Biosystems Inc., U.S.A.), the sample is subjected to Edman degradation from the N-terminus in accordance with the method of R. M. Hewick et al [J. Biol. Chem., 256, 7990–7997 (1981)]. Phenylthiohydantoin amino acid liberated is analyzed by the conventional method by means of a high performance liquid chromatography model SP8100 (manufactured and sold by Spectra Physics, U.S.A.) using Zorbax ODS (manufactured and sold by E. I. Du Pont, U.S.A.) as the column to determine the N-terminal amino acid sequence of the present substance.

ITEM (2) DETERMINATION OF MOLECULAR WEIGHT (A) Gel filtration method

According to the method of P. Andrews [Biochem. J., 96, 595–606 (1965)], the molecular weight in terms of a value as measured by a gel filtration method is determined as follows.

Using a column (1.5×100 cm) of Sephacryl S-200 (produced by Pharmacia Fine Chemicals AB, Sweden), gel filtration is performed with 0.05M phosphate buffer, pH 7.4, containing 0.1M NaCl. Calibration of the molecular weight is conducted by the use of standard proteins, ribonuclease A, chymotrypsinogen A, ovalbumin and aldolase (produced by Pharmacia Fine Chemicals AB, Sweden) to obtain a molecular calibration pattern. The peak exhibiting the cytotoxic activity against L-M cells is compared with the molecular calibration pattern, thereby to determine the molecular weight of the protein of the present invention.

(B) SDS-polyacrylamide gel electrophoresis method

According to the method of Segrest et al [V. Ginsburg (ed.), "Methods in Enzymology," Vol. 28-B, Academic Press Inc., New York, 1972, pp. 54–63], 10 μg of a sample of the present substance is applied to 12.5% SDS (sodium dodecyl sulfate)-polyacrylamide gel and electrophoresis is carried out at 120 V in SDS/Tris [tris(hydroxymethyl)aminomethane]-glycine buffer (pH 8.3). The resulting gel is stained with Coomassie Brilliant Blue R-250 to give stained bands. On the other hand, calibration of the molecular weight is conducted by the use of a standard molecular weight kit (produced by Pharmacia Fine Chemicals AB, Sweden) to obtain a molecular calibration pattern. By evaluation of the exhibited cytotoxic activity against L-M cells and comparison of the stained bands with the molecular calibration pattern, there is obtained a molecular weight of the desired protein of the present invention.

ITEM (3) DETERMINATION OF ISOELECTRIC POINT

The isoelectric point is determined using an apparatus for isoelectric electrophoresis SJ-1071 (manufactured and sold by Atto Co., Ltd., Japan). On a 5% polyacrylamide gel plate (thickness: 1 mm, length: 10 cm, width: 10 cm) containing carrier ampholytes, Pharmalite (produced by Pharmacia Fine Chemicals AB, Sweden; pH 4-6.5) and glycerol using 0.04M DL-glutamic acid on the side of the anode and 0.2M L-histidine on the side of the cathode the formation of pH gradient is effected at 700 V for 50 minutes. Then, 50 μg of a sample is applied to the polyacrylamide gel plate, and migration is conducted at 700 V for 1 hour and subsequently, at 500 V for 16 hours. After completion of the electrophoresis, strips each having a width of 2.5 mm are prepared from the gel and each strip is then subjected to extraction with 0.2 ml of 0.02M Tris-HCl buffer solution (pH 8.2) containing 0.15M NaCl. With respect to the thus obtained each extract, evaluation of cytotoxic activity against L-M cells is effected to determine the isoelectric point of the sample.

ITEM (4) EVALUATION OF CYTOTOXIC ACTIVITY AGAINST L-M CELLS

The evaluation of the cytotoxic activity of the protein of the present invention against L-M cells (American Type Culture Collection CCL 1.2) is effected in accordance with the method developed by modifying the methods of Ruff et al [E. Pick (ed.), "Lymphokines," Vol. 2; Academic Press Inc., New York, 1980, pp. 245-248] and Kull et al [J. Immunol., 126, 1279-1283 (1981)]. The method of the evaluation of the cytotoxic activity of the present substance is explained below.

As culture vessels, there are employed 96-well microtiter plates produced by Flow Laboratories, Inc. (U.S.A.) and L-M cells are cultured in Eagle's minimum essential medium [see Science, 130, 432-437 (1959)] containing 1 v/v% fetal calf serum. A sample (0.1 ml) of the present substance serially diluted with the medium and the L-M cell suspension ($1 \times 10^4$ cells) are mixed in each well of the plates and the plates are incubated at 37° C. for 48 hours in air containing 5% carbon dioxide. At the end of the culture period, a 20% aqueous solution of glutaraldehyde (20 μl) is added to fix the cells. After fixation, the plates are washed with distilled water and allowed to dry, and 0.05% methylene blue (0.1 ml) is added to stain the viable cells. The plates are thoroughly washed with distilled water to remove excess dye and allowed to dry. To each well is added 0.36N hydrochloric acid (0.2 ml) to extract the dye from stained cells. Absorbance of each well at 665 nm is measured with Titertek Multiskan (produced by Flow Laboratories, Inc. U.S.A.). The absorbance is proportional to the number of viable cells. The cytotoxic activity of the sample unit/ml, is defined as the reciprocal dilution of the sample that causes 50% cytotoxicity, and can be obtained by plotting the dilution versus the absorbance on a graph. The "1 unit" used herein means a quantity of the present substance by which 50% of $1 \times 10^5$ cells/ml of L-M cells are killed.

On the other hand, the amount of protein is determined by a method in which Coomassie Brilliant Blue G250 is bonded to protein, according to the teaching of Brandford et al [see Anal. Biochem. 72, 248-254 (1976)].

ITEM (5) TUMOR NECROTIC EFFECT ON METH A SARCOMA TRANSPLANTED IN MICE

BALB/c sarcoma Meth A cells ($2 \times 10^5$ cells) are transplanted intradermally at the abdomen of each of BALB/c mice and, 7 days later, mice with tumors of 7-8 mm in diameter, good vascularization and no spontaneous central necrosis are selected for examining the tumor necrotic effect of the present substance. The present substance is dissolved in a physiological saline solution in each amount of 3000, 5000, 10000 and 20000 units/0.2 ml. The solution of the present substance (0.2 ml) is injected through the tail vein of each of the mice. The activity of the sample is evaluated after 24 hours according to the following criterion.

(−): no change
(+): slight hemorrhagic necrosis
(++): moderate hemorrhagic necrosis (central necrosis extending over approximately 50% of the tumor surface)
(+++): marked hemorrhagic necrosis (massive necrosis leaving a small viable rim along the tumor periphery)

20 Days after the injection of the sample, observations are made on the involution of tumors and recovery rate is determined according to the following equation.

$$\text{Cured ratio} = \frac{\text{Number of mice cured completely}}{\text{Number of mice used for test}}$$

The results are shown in Table 1 below.

TABLE 1

| Dose of the present substance (units/mouse) | Number of mice used for test | Necrotic response − | + | ++ | +++ | Cured Ratio |
|---|---|---|---|---|---|---|
| 3,000 | 6 | 3* | 3 | 0 | 0 | 1/6 |
| 5,000 | 6 | 2 | 1 | 3 | 0 | 2/6 |
| 10,000 | 6 | 0 | 1 | 2 | 3 | 3/6 |
| 20,000 | 6 | 0 | 0 | 1 | 5 | 6/6 |
| Control (Physiological saline) | 6 | 6 | 0 | 0 | 0 | 0/6 |

Note:
*Number of mice

ITEM (6) MOBILITY IN CELLULOSE ACETATE MEMBRANE ELECTROPHORESIS

Using cellulose acetate membrane (Separax-S, product of Fuji Photo Film Co., Ltd., Japan), a sample of the present substance is subjected to electrophoresis. The electrophoresis is performed in barbiturate buffer of pH 8.6 and ionic strength of 0.06 to 0.07. After completion of the electrophoresis, the membrane is cut into 1-mm slices. Each slice is subjected to extraction with a physiological saline solution. Thus thus obtained each extract is subjected to evaluation of cytotoxic activity against L-M cells to determine the mobility. Another sample of the present substance is subjected to electrophoresis under the same conditions as mentioned above for protein staining with Ponceau-3R (produced by Nakarai Chemicals, Ltd., Japan). The stained band position of the present substance is compared with that of α-globulin.

ITEM (7) INFLUENCE OF TREATMENT WITH A REDUCING AGENT

Using dithiothreitol (0.1 mM, 1 mM) or 2-mercaptoethanol (0.1 mM, 1 mM) as a reducing agent for disulfide bond, 20 µg/ml of the present substance is reacted with a reducing agent for disulfide bond in 0.15 M NaCl/0.05M phosphate buffer solution (pH 7.4) at 25° C. for 2 hours. After completion of the reaction, the resulting reaction mixture is subjected to evaluation with respect to cytotoxic activity against L-M cells. On the other hand, substantially the same procedures as mentioned above are repeated except that any reducing agent for disulfide bond is not used to determine the cytotoxic activity of the reaction mixture (control) against L-M cells. The remaining cytotoxic activity (%) of the reaction mixture (which has been obtained by reacting the present substance with a reducing agent) against L-M cells is calculated according to the following equation:

Remaining activity (%) = A/B × 100

(wherein A is the cytotoxic activity of the reaction mixture against L-M cells, and B is the cytotoxic activity of the control mixture against L-M cells) The results are shown in Table 2.

TABLE 2

| Reducing agent | Concentration | Remaining activity |
| --- | --- | --- |
| Dithiothreitol | 0.1 mM | 97% |
|  | 1 mM | 102% |
| 2-Mercaptoethanol | 0.1 mM | 98% |
|  | 1 mM | 99% |

ITEM (8) ADSORBABILITY ON LECTIN COLUMN

Various kinds of immobilized lectins indicated in Table 3 are packed separately into minicolumns (Econo-Column, product of Bio-Rad Laboratories, U.S.A.). Each column is thoroughly washed with 0.05M phosphate buffer solution (pH 7.5) containing 0.15M NaCl. Then, 100 µg of the present substance dissolved in the above-mentioned buffer solution is applied to each column. After washing the column with the above-mentioned buffer solution, elution is conducted using various eluents as indicated in Table 3. A passed-through fraction and eluate fractions thus obtained are evaluated with respect to a cytotoxic activity against L-M cells to determine the adsorbability of the present substance.

TABLE 3

| Column employed | Eluent |
| --- | --- |
| Con A-Sepharose (Pharmacia Fine Chemicals AB, Sweden) | 0.1 M α-methyl-D-mannoside |
| WGA-Sepharose 6MB (Pharmacia Fine Chemicals AB, Sweden) | 0.1 M N—acetyl-D-glucosamine |
| RCA-I-gel (E.Y. Laboratories, U.S.A.) | 0.1 M lactose |
| UEA-I-gel (E.Y. Laboratories, U.S.A.) | 0.05 M α-L-fucose |
| LPA-I-gel (E.Y. Laboratories, U.S.A.) | 0.1 M sialic acid |

As mentioned before, the present substance has a molecular weight of 40,000±5,000 in terms of a value as measured by the gel filtration method, whereas, the measurement of the molecular weight of the present substance by the SDS-polyacrylamide gel electrophoresis method gives a molecular weight of 17,500±2,000. In this connection, it is noted that when the protein is subjected to SDS-polyacrylamide gel electrophoresis, the protein dissociates into polypeptide subunits. Therefore, from the above-mentioned facts, it is confirmed that the present substance comprises a polypeptide subunit. The term "polypeptide subunit" used herein means a polypeptide chain which is associated with other polypeptide chains by non-covalent bond to form a protein.

The protein of the present invention may be produced by preparing a crude solution containing the protein of the present invention from rabbit, and subjecting the thus prepared crude solution to purification. The method for the production of the present substance will now be described in detail. In the following description, it is noted that the concentration (mg/ml) of the total protein including the present substance and the concentration (units/ml), in terms of the cytotoxic activity against L-M cells, of the present substance of the crude solutions and fractions obtained by purifying the crude solutions are measured in accordance with the protein assay method and the activity evaluation method using L-M cells, respectively. With respect to the details of the protein assay method and the activity evaluation method, reference is made to item (4) of the property-determining method described before.

PREPARATION OF A CRUDE SOLUTION CONTAINING THE PRESENT SUBSTANCE

A crude solution containing the present substance may be prepared by administering to a rabbit at least one substance capable of stimulating the reticuloendothelial system and then injecting endotoxin from a Gram-negative bacterium into the rabbit, and taking the body fluid and/or serum or plasma of the rabbit or extracting internal organs of the rabbit with a physiological saline solution. The method for the above-mentioned preparation of the crude solution is explained below. First, at least one substance capable of stimulating the reticuloendothelial system is injected intravenously or intraperitoneally into a rabbit. As the substances capable of stimulating the reticuloendothelial system, there may generally be used Gram-positive bacteria, protozoas or yeasts, which are administered to the rabbit in the form of either of living microorganisms, dead microorganisms (e.g. after heat treatment or formalin treatment) and microorganism cell extracts. Examples of the Gram-positive bacteria include Propionibacteria such as *Propionibacterium acnes* (*Corynebacterium parvum*) and *Propionibacterium granulosum* (*Corynebacterium granulosum*), Mycobacteria such as bacillus Calmette-Guérin (BCG) and *Mycobacterium smegmatis*, and Nocardias such as *Nocardia erythropolis* and *Nocardia gardneri*. As a suitable protozoa, for example, Plasmodium or Toxoplasma is employable. As a suitable yeast, Zymosan extracted from *Saccharomyces cerevisiae* or others is generally used. There may also be employable synthetic high molecular compounds such as pyran copolymer. When as the substance capable of stimulating the reticuloendothelial system *Propionibacterium acnes* is used, it is preferred that the substance be intravenously administered to rabbit at a dose of generally about 20 to 400 mg/adult rabbit, preferably about 50 to 200 mg/adult rabbit. When BCG is used as the substance capable of stimulating the reticuloendothelial system, it is preferred that the BCG be intravenously administered to rabbit in an amount of about $5 \times 10^7$ to $30 \times 10^7$ cells/adult rabbit in the viable state. Second, 7 to 14 days after administration of the above-mentioned substance capable of stimulating the reticuloendothelial system, endotoxin from a Gram-negative bacterium, for example, a lipopolysaccharide derived from *Escherichia coli, Pseudomonas aeruginosa*, or *Salmonella typhosa* is injected intravenously into said rabbit. The endotoxin is injected to the rabbit at a dose of generally about 20 to 400 μg, preferably about 50 to 200 μg/adult rabbit. Third, 1.5 to 2 hours after the injection of endotoxin, body fluids (e.g. ascites, lymph, etc.) and/or serum or plasma of said rabbit are taken or internal organs such as liver, spleen, etc. are homogenized and extracted with a physiological saline solution. The above-mentioned body fluids, serum, plasma and/or extract of internal organs may be employed as the crude solution of the present substance. Of them, however, serum or plasma is generally employed.

Alternatively, the crude solution containing the present substance may also be prepared by adding endotoxin from a Gram-negative bacterium to a tissue culture of macrophages from a rabbit and incubating the resulting culture. As the macrophages, there may be employed, for example, macrophages obtained from alveolus, peripheral blood, peritoneal exudate, spleen, liver and the like of a normal rabbit or a rabbit which has been administered at least one substance capable of stimulating the reticuloendothelial system in the same manner as described above. To effect culturing of the macrophage, any of culture media usually employed for tissue culture may be employed. As examples of the culture media, there may be mentioned Eagle's minimum essential medium (hereinafter often referred to as "Eagle's MEM"), RPMI-1640 and the like. As the endotoxin from Gram-negative bacteria, the same endotoxins as those mentioned before may be employed. The endotoxin may be added to the culture of the macrophage generally in an amount of about 0.1 to 1000 μg/ml (final concentration), preferably about 1 to 100 μg/ml. After addition of the endotoxin, the culture is incubated for about 3 to 48 hours, thereby to liberate the present substance in the supernatant of the culture. The supernatant is taken as a crude solution containing the present substance, and subjected to subsequent purification.

Among the above-mentioned crude solutions containing the present substance, serum or plasma may most preferably be employed.

PURIFICATION OF THE CRUDE SOLUTION CONTAINING THE PROTEIN OF THE PRESENT INVENTION

The method of purification of the crude solution containing the present substance includes the steps of:
(a) pre-treatment,
(b) basic anion exchanger chromatography
(c) heat treatment, then in either order,
(d) gel filtration, and
(e) zinc chelate affinity chromatography, and, if desired,
(f) gel filtration The above steps (a) to (f) for purification of the present substance will be described below in detail. In the following description, the activity recovery is determined by the following equation:

$$\text{Activity recovery (\%)} = \frac{\text{Total amount (units) of the present substance in the solution or fraction obtained in each of the purification steps}}{\text{Total amount (units) of the present substance in the crude solution}} \times 100$$

Note:
The amount (units) of the present substance is given in terms of cytotoxic activity against L-M cells.

Further, the purity increase used herein is determined by the following equation:

$$\text{Purity increase (fold)} = \frac{\text{Purity (units/mg-protein) of the present substance in the solution or fraction obtained in each of the purification steps}}{\text{Purity (units/mg-protein) of the present substance in the crude solution}}$$

Note:
The amount (units) of the present substance is given in terms of cytotoxic activity against L-M cells.

STEP (a)

The crude solution obtained above is subjected to treatment with a chelating agent and diatomaceous earth powder, followed by filtration using a filter, thereby to obtain a filtrate. As a suitable chelating agent, there may be mentioned, for example, ethylenediaminetetraacetic acid disodium salt. As the diatomaceous earth powder, there may be mentioned, for example, Celite, Super-cell (produced by John-Manville Sales Corp., U.S.A.) and the like. The filtration may be conducted using a filter or several kinds of filters in combination. The or each filter has a pore size of 0.2 to 3 μm. The activity recovery of the present substance through the step (a) is about 95 to 100%.

STEP (b)

The filtrate obtained in step (a) above is contacted with a basic anion exchanger using a buffer solution of pH 6.0 to 8.0 and of a salt concentration of 0.2M or lower, so that the present substance is adsorbed on the anion exchanger. Subsequently, said anion exchanger is washed with the same buffer solution to remove the unadsorbed proteins and, thereafter, the present substance is eluted using a buffer solution of a higher salt concentration. The contact of the filtrate with a basic anion exchanger may be conducted either by column chromatography or a batchwise method. Before the contact is performed, the filtrate may be dialyzed against the buffer solution to be used at the time of contacting with the anion exchanger or it may be diluted with a buffer solution having a lower salt concentration.

Preferred examples of suitable basic anion exchangers used include anion exchangers containing diethylamino groups such as DEAE-Sephadex A-50, DEAE-Sepharose CL-6B and DEAE-Sephacel (all produced by Pharmacia Fine Chemicals AB, Sweden). The suitable buffer solutions used include a dilute Tris-hydrochloric acid buffer, a dilute phosphate buffer and the like. Sodium chloride or potassium chloride is preferably added to adjust a salt concentration of the buffer solution.

If the purity increase attained in step (b) is less than 600-fold, the purification of this step (b) is repeated.

STEP (c)

The fraction of the present substance obtained in step (b) above is concentrated by means of ultrafiltration, lyophilization or chromatography using a basic anion exchanger column of appropriate volume. Then, the resulting fraction is subjected to heat treatment at 60° C. to 70° C. for a period of 30 minutes to 2 hours, preferably at 60° C. for 30 minutes. As suitable examples of the buffer solution to be used in the heat treatment, there may be mentioned, for example, Tris-hydrochloric acid buffer solution, phosphate buffer solution and the like (pH 6.0–9.0). After completion of the heat treatment, the fraction is concentrated by means of ultrafiltration, lyophilization or chromatography using a basic anion exchanger column of appropriate volume. The overall activity recovery, of the present substance, attained by steps (a) through (c) are about 78 to 100%, with the purity increase being 600-fold or more.

STEP (d)

The concentrate obtained in step (c) is subjected to gel filtration using a gel suitable for separation of a substance with a molecular weight of 30,000 to 70,000. As an eluent, there is employed a buffer solution having a pH of generally 6.0 to 9.0. The salt concentration of the buffer is 1.0M or lower. The suitable gels for gel filtration include Sephadex G-150 or G-200, Sephacryl S-200 (all produced by Pharmacia Fine Chemicals AB, Sweden), Bio-Gel P-150 or P-200 (produced by Bio-Rad Co., U.S.A.), TOYOPEARL HW-55 or HW-65 (produced by Toyo Soda Mfg. Co., Ltd., Japan) and the like. Examples of the buffer solution and the salt to be employed in this step (d) are the same as those described above in step (b). The fractions containing the present substance are collected, and concentrated by ultrafiltration, lyophilization or chromatography on a small column packed with a basic anion exchanger. The overall activity recovery, of the present substance, attained by steps (a) through (d) is about 70 to 95%, with the purity increase being about $1 \times 10^4$ to $4 \times 10^4$-fold.

STEP (e)

The fraction obtained in step (d) is subjected to affinity chromatography using a $Zn^{2+}$ chelate sepharose column prepared according to the method of J. Porath et al. [Nature, 258, 598–599 (1975)]. Instead of the above-mentioned column, there may be used a column packed with Sepharose CL-6B coupled with iminodiacetic acid (iminodiacetic acid-Sepharose CL-6B) (manufactured and sold by Pharmacia Fine Chemicals AB, Sweden). In the latter case, an aqueous zinc chloride solution having a zinc chloride concentration of 1 mg/ml is applied to iminodiacetic acid-Sepharose CL-6B column, thereby to cause $Zn^{2+}$ to be chelation-adsorbed onto iminodiacetic acid-Sepharose Cl-6B. After washing the column with an elution buffer, the fractions obtained in step (d) are applied, as such or in the form of a concentrate, to the column. The buffer employed in this step is the same as that described in step (b). By the above-mentioned procedure, most of contaminating proteins in the fractions obtained in step (d) are adsorption-removed, and the present substance is eluted as unadsorbed fractions. The overall activity recovery, of the present substance, attained by steps (a) through (e) is about 56 to 76%, with the purity increase being about $2 \times 10^4$ to $7 \times 10^4$-fold.

STEP (f)

The solution containing the present substance obtained in step (e) is subjected to gel filtration using the same buffer, salt and gel as employed in step (d). However, the length and the diameter of the column to be used in this step are respectively longer and smaller than those of the column employed in step (d). The active fractions are pooled and concentrated, and if necessary, dialyzed, sterilized by filtration and lyophilized to provide the present substance. The overall activity recovery, of the present substance, attained by steps (a) through (f) is about 50 to 70%, with the purity increase being about $4 \times 10^4$ to $1.5 \times 10^5$-fold.

The step (c) is very important in the process of producing the present substance. Without purification by step (c), sufficient separation of the present substance from other proteins as impurities which cause the present substance to be instable cannot be attained and, therefore, the stable present substance cannot be obtained. Further, the heat treatment effected in step (c) imparts heat stability to the present substance.

The above-mentioned steps (a) to (f) may preferably be conducted in the above-mentioned order. However, steps (d) and (e) may be conducted in either order. If the sufficiently purified present substance can be obtained by purification of steps (a) to (e), the step (f) may be omitted.

Thus, according to the above-mentioned process, the present protein is obtained in substantially pure form at high activity recovery.

The novel protein of the present invention induces necrosis of tumors with substantially no species specificity. Also, the protein of the present invention thus obtained is excellent in stability and, therefore, the present substance can be obtained from the crude solution at an activity recovery as high as about 50 to 70%. Further, the present substance is excellent in heat stability. Therefore, when preparation of pharmaceutical compositions is conducted according to known methods as described later, the substantially pure substance of the present invention can be stably formulated into compositions.

The substantially pure substance of the present invention is very effective for the treatment of mammalian (including human) malignant tumor as an antitumor agent. The present substance may be combined in admixture with a pharmaceutically acceptable carrier vehicle well known in the art. An effective amount of the protein of the present invention may be mixed with a suitable amount of inorganic or organic, solid or liquid carrier vehicle which is unreactive with the present substance in order to prepare pharmaceutically acceptable compositions suitable for effective administration to the recipient. The pharmaceutical compositions may be in the form of solid, semi-solid or liquid dosage forms, such as, for example, tablets, capsules, granules, fine granules, powders, liquids, suspensions, suppositories, or the like, but preferably in unit dosage forms suitable for single administration of precise dosage. The present substance may preferably be used in the form of liquid compositions for parenteral or topical administration. Such compositions are preferably in the form of isotonic aqueous solutions or suspensions which can be prepared before use, for example, from lyophilized preparations which contain the present substance alone or together with a pharmaceutically acceptable carrier. The pharmaceutical preparations may, if desired, contain nontoxic auxiliary substances such as stabilizers (e.g. human serum albumin, gelatin, polyoxyethylene hydrogenated castor oil and the like), isotonic agents (e.g. sodium chloride and the like), buffering agents (e.g. a phosphate, a carbonate and the like), preservatives, solubilizers, wetting or emulsifying agents and the like.

Accordingly, in a further aspect of the present invention, there is provided a pharmaceutical composition comprising an effective antitumor amount of the present substance and at least one pharmaceutically acceptable carrier, diluent or excipient.

The protein of the present invention may be administered, to subjects requiring antitumor treatment, as an oral administration, parenteral administration, topical administration or rectal administration. The clinical dosage of the protein of the present invention may vary depending on the route of administration, and the condition and the body weight of the patient, but may be generally about $10^3$ to $10^8$ units per one administration for an adult human. The protein of the present invention may also be administered together with other antitumor agents such as cyclophosphamide, mitomycin C, adriamycin and bleomycin.

The term "1 unit" used above means a quantity of the protein of the present invention by which 50% of $1 \times 50^5$ cells/ml of L-M cells (American Type Culture Collection CCL 1.2) are killed. The above-mentioned quantity is measured in the same manner as described in item (4) entitled "Evaluation of cytotoxic activity against L-M cells."

The protein of the present invention has an excellent anticancer effect on various murine tumors transplanted to syngeneic mice or human cancers transplanted to nude mice. For example, in the case of murine tumors, significant growth inhibition or regression of tumors was observed after one, two or three intravenous injections of 5,000–10,000 units of the present substance, as compared with control mice which were injected with a physiological saline solution, in the following mice: BALB/c mice transplanted with adenocarcinoma Colon 26, C57BL/6 mice transplanted with malignant melanoma B16, or A mice transplanted with neuroblastoma Neuro-2a. As to human cancers, significant growth inhibition or regression was observed after 1 to 7 intravenous injections of 10,000–30,000 units of the present substance, as compared with control mice which were injected with a physiological saline solution, in the nude mice which had been transplanted with human lung cancer PC-10, malignant melanoma HMV-2 or neuroblastoma GOTO.

Accordingly, in a further aspect of the present invention, there is provided a method for treating tumors by administering to a host an effective antitumor amount of the present substance.

The present invention is illustrated in detail with reference to the following Example, which should not be construed to be limiting the scope of the present invention.

EXAMPLE 400 female rabbits of Nihon-hakushokushu (Japanese white) (Nihon Seibutsu Zairyo Center K.K., Japan), each weighing from 2.5 to 3.0 kg, were each injected intravenously with 50 mg of formalin-killed cells of Propionibacterium acnes (Corynebacterium parvum, Welcome Research Laboratories, England). Eight days later, the rabbits were each injected intravenously with 100 μg of endotoxin (lipopolysaccharide from Escherichia coli 026: B6, produced by Difco Laboratories, U.S.A.). The blood was obtained from each rabbit by cardiac puncture 2 hours after the injection of endotoxin, and the blood obtained was mixed with 1 unit/ml of sodium heparinate. The blood was centrifuged at 5,000 rpm for 30 minutes to remove blood cells and insoluble solids. As a result, 24 liters of plasma having an activity of 3,000 units/ml was obtained from 400 rabbits.

Purification step (a) (pre-treatment)

To the plasma (24 liters) obtained above were added 24 g of disodium ethylenediaminetetraacetate and 240 g of Celite. The thus obtained mixture was stirred for one hour and subjected to filtration successively through filters each having a pore size of 3 μm, 1 μm and 0.2 μm.

Purification step (b) (basic anion exchanger chromatography)

The filtrate (24 liters) obtained above was diluted with 12 liters of 0.04M Tris-HCl buffer, pH 7.8. The diluted filtrate was applied slowly to a column (27×45 cm) of DEAE-Sepharose CL-6B (Pharmacia Fine Chemicals AB, Sweden) equilibrated with 0.04M Tris-HCl buffer, pH 7.8, containing 0.1M NaCl. The column was washed with 75 liters of 0.04M Tris-HCl buffer, pH 7.8, containing 0.1M NaCl and then washed with 50 liters of 0.04M Tris-HCl buffer, pH 7.8, containing 0.15M NaCl. The elution was carried out with 0.04M Tris-HCl buffer, pH 7.2, containing 0.18M NaCl at a flow rate of 5 liters/hr to obtain 8 liters of active fractions. The active fractions were pooled and diluted with an equal volume of 0.04M Tris-HCl buffer, pH 7.8. The diluted solution was applied at a flow rate of 2 liters/hr to a column (10×13 cm) of DEAE-Sepharose CL-6B. The column was washed at a flow rate of 200 ml/hr with one liter of 0.04M Tris-HCl buffer, pH 7.8, containing 0.1M NaCl and then eluted with 5 liters of 0.04M Tris-HCl buffer, pH 7.2, containing 0.18M NaCl. The flow rate was 200 ml/hr and 250-ml fractions were collected. The active fractions were pooled. The activity recovery obtained by this step was 90%, with the purity increase being 660-fold.

Purification step (c) (heat treatment)

The fraction obtained above was charged into a vessel. The vessel was heated on a water bath held at 70° C. while stirring until the temperature of the fraction reached 60° C. The vessel was transferred onto another water bath heated at 60° C. The vessel was heated on it for 30 minutes and then rapidly cooled to 4° C. The cooled solution was concentrated by ultrafiltration. The overall activity recovery obtained by the purification steps (a) to (c) was 88%.

Purification step (d) (gel filtration)

The concentrate obtained above was applied to a column (5×80 cm) of Sephacryl S-200 (Pharmacia Fine Chemicals AB, Sweden) equilibrated with 0.005M phosphate buffer, pH 7.4, containing 0.1M NaCl. The gel filtration elution was effected using the same buffer at a flow rate of 40 ml/hr. The fractions each of 40 ml were collected to obtain active fractions. The active fractions were pooled and concentrated by ultrafiltration. The overall activity recovery obtained by the purification steps (a) to (d) was 82%, with the purity increase being $2.0 \times 10^4$-fold.

Purification step (e) (zinc chelate affinity chromatography)

The concentrate obtained above was subjected to $Zn^{2+}$-chelate-Sepharose CL-6B column chromatography in a manner described below.

Fifteen grams of Epoxy-activated Sepharose CL-6B (produced by Pharmacia Fine Chemicals AB, Sweden) was swollen for 2 hours in 100 ml of distilled water. The swollen gels were collected on a glass filter by suction filtration, washed thoroughly with distilled water, and suction-dried. The thus obtained gels were suspended in 30 ml of 2M aqueous sodium carbonate solution containing 6 g of disodium salt of iminodiacetic acid. The suspension was heated at 65° C. for 24 hours while shaking gently. The reaction product was collected on a glass filter by suction filtration to obtain iminodiacetic acid-Sepharose CL-6B (45 ml). The thus obtained gels were charged into a column (1.6×20 cm). Through the thus prepared column 120 ml of aqueous zinc chloride solution ($ZnCl_2$ 1 mg/ml) was passed at a flow rate of 20 ml/hr, thereby to obtain $Zn^{2+}$-chelate-Sepharose CL-6B. The concentrate obtained by the purification step (d) was applied, at a flow rate of 20 ml/hr, to the $Zn^{2+}$-chelate-Sepharose CL-6B column equilibrated with 0.05M phosphate buffer, pH 7.4, containing 0.1M NaCl. The unadsorbed fractions eluted with 120 ml of the equilibrating buffer were pooled. Most of the activity was recovered in the unadsorbed fractions. The overall activity recovery obtained by the purification steps (a) to (e) was 66%, with the purity increase being $5.0 \times 10^4$-fold.

Purification step (f) (gel filtration)

The active fractions obtained in the above step 5 were concentrated by ultrafiltration and applied to a column (1.5×90 cm) of TOYOPEARL HW-55 (manufactured and sold by Toyo Soda Mfg. Co., Ltd., Japan) equilibrated with 0.005M phosphate buffer, pH 7.4, containing 0.15M NaCl. The gel filtration elution was carried out with the same buffer at a flow rate of 4 ml/hr to obtain active fractions. The active fractions were pooled and concentrated by ultrafiltration. The overall activity recovery obtained by the purification steps (a) to (f) was 60%, with the purity increase being $7.5 \times 10^4$-fold. The thus obtained substance was found to have a specific activity of $6.0 \times 10^6$ units/mg-protein in terms of a value as measured by item (4) of the property-determining method as mentioned above.

What is claimed is:

1. A protein having an antitumor activity comprising a polypeptide subunit having an N-terminal amino acid sequence of the following formula (I):

Ser-Ala-Ser-Arg-Ala-Leu-Ser-Asp-Lys-Pro-Leu-Ala-His-Val-Val-Ala-Asn-Pro-Gln-Val-Glu-Gly-Gln-Leu-Gln-Trp-Leuwherein Ala stands for alanine residue, Arg an arginine residue, Asn an asparagine residue, Asp an aspartic acid residue, Gln a glutamine residue, Glu a glutamic acid residue, Gly a glycine residue, His a histidine residue, Leu a leucine residue, Lys a lysine residue, Pro a proline residue, Ser a serine residue, Trp a tryptophan residue and Val a valine residue;

and which protein has:

(a) a molecular weight of 40,000±5,000 in terms of a value as measured by a gel filtration method as defined herein and a molecular weight of 17,500±2,000 in terms of a value as measured by an SDS-polyacrylamide gel electrophoresis method as defined herein; and (b) an isoelectric point of 5.0±0.3 in terms of a value as measured by an isoelectric focusing method as defined herein.

2. A substantially pure protein having an antitumor activity comprising the polypeptide subunit having the N-terminal amino acid sequence as defined in claim 1.

3. A pharmaceutical composition comprising an effective antitumor amount of a protein of claim 1 and at least one pharmaceutically acceptable carrier, diluent or excipient.

4. A pharmaceutical composition comprising an effective antitumor amount of a protein of claim 2 and at least one pharmaceutically acceptable carrier, diluent or excipient.

5. A method for treating tumors by administering to a host an effective antitumor amount of a protein of claim 1.

* * * * *